US009949915B2

(12) United States Patent
Rubin et al.

(10) Patent No.: US 9,949,915 B2
(45) Date of Patent: Apr. 24, 2018

(54) NON-COMEDOGENIC AND NON-ACNEGENIC HAIR AND SCALP CARE FORMULATIONS AND METHOD FOR USE

(71) Applicant: Clarity Cosmetics Inc., Potomac, MD (US)

(72) Inventors: Iris Rubin, Potomac, MD (US); Gregory Maged, Bethesda, MD (US); John Garruto, Encinitas, CA (US); Bethany McCarver, Oceanside, CA (US)

(73) Assignee: CLARITY COSMETICS INC., Potomac, MD (US)

( * ) Notice: Subject to any disclaimer, the term of this patent is extended or adjusted under 35 U.S.C. 154(b) by 0 days.

(21) Appl. No.: 15/618,420

(22) Filed: Jun. 9, 2017

(65) Prior Publication Data
US 2017/0354585 A1 Dec. 14, 2017

Related U.S. Application Data

(60) Provisional application No. 62/348,510, filed on Jun. 10, 2016.

(51) Int. Cl.

| | | |
|---|---|---|
| *A61Q 5/00* | (2006.01) | |
| *A61K 8/72* | (2006.01) | |
| *A61K 8/73* | (2006.01) | |
| *A61Q 5/02* | (2006.01) | |
| *A61K 8/34* | (2006.01) | |
| *A61K 8/81* | (2006.01) | |
| *A61K 8/46* | (2006.01) | |
| *A61K 8/42* | (2006.01) | |
| *A61K 8/31* | (2006.01) | |
| *A61K 8/41* | (2006.01) | |
| *A61Q 5/12* | (2006.01) | |
| *A61K 8/365* | (2006.01) | |
| *A61K 8/37* | (2006.01) | |
| *A61Q 5/06* | (2006.01) | |

(52) U.S. Cl.
CPC ............... *A61K 8/737* (2013.01); *A61K 8/31* (2013.01); *A61K 8/34* (2013.01); *A61K 8/342* (2013.01); *A61K 8/345* (2013.01); *A61K 8/347* (2013.01); *A61K 8/365* (2013.01); *A61K 8/37* (2013.01); *A61K 8/41* (2013.01); *A61K 8/416* (2013.01); *A61K 8/42* (2013.01); *A61K 8/463* (2013.01); *A61K 8/817* (2013.01); *A61K 8/8141* (2013.01); *A61Q 5/02* (2013.01); *A61Q 5/06* (2013.01); *A61Q 5/12* (2013.01); *A61K 2800/30* (2013.01)

(58) Field of Classification Search
None
See application file for complete search history.

(56) References Cited

U.S. PATENT DOCUMENTS

| | | |
|---|---|---|
| 5,863,546 A | 1/1999 | Swinehart |
| 6,312,675 B1 | 11/2001 | Deane |
| 6,406,708 B1 | 6/2002 | Karnerud et al. |
| 6,723,309 B1 | 4/2004 | Deane |
| 6,923,954 B2 | 8/2005 | Doi et al. |
| 7,182,939 B2 | 2/2007 | Tajima et al. |
| 7,326,410 B2 | 2/2008 | Doi et al. |
| 7,691,792 B1 | 4/2010 | Fisher et al. |
| 8,092,813 B1 | 1/2012 | Novicki |
| 8,173,143 B2 | 5/2012 | Tecco et al. |
| 8,309,143 B2 | 11/2012 | Campbell et al. |
| 8,586,814 B2 | 11/2013 | Fisher et al. |
| 8,628,786 B2 | 1/2014 | Novicki |
| 8,957,112 B2 | 2/2015 | Mallard et al. |
| 9,271,956 B2 | 3/2016 | Auclair |
| 9,370,570 B2 | 6/2016 | Novicki |
| 9,757,317 B2 | 9/2017 | Laughlin, II et al. |
| 2002/0143063 A1 | 10/2002 | Alvarado |
| 2003/0039619 A1 | 2/2003 | Bunger et al. |
| 2004/0186042 A1 | 9/2004 | Schmaus et al. |
| 2004/0258651 A1 | 12/2004 | Pascaly et al. |
| 2004/0258652 A1 | 12/2004 | Pascaly et al. |
| 2006/0057075 A1 | 3/2006 | Arkin et al. |
| 2007/0082017 A1 | 4/2007 | Tseng |
| 2007/0166241 A1 | 7/2007 | Baker |
| 2007/0286838 A1* | 12/2007 | Axelrod ................. A61K 8/361 424/74 |
| 2008/0275118 A1 | 11/2008 | Shaw et al. |
| 2009/0226381 A1 | 9/2009 | Maillefer et al. |

(Continued)

FOREIGN PATENT DOCUMENTS

| | | |
|---|---|---|
| EP | 1077675 B1 | 8/2005 |
| EP | 1693050 B1 | 7/2012 |

(Continued)

OTHER PUBLICATIONS

L Lanuzo. "Sebamed Everyday Shampoo for Normal to Dry Hair and Scalp." http://www.projectvanity.com/projectvanity/2011/10/27/sebamed-everyday-shampoo-for-normal-to-dry-hair-and-scalp.html, accessed Dec. 22, 2017, originally published Oct. 27, 2011, 8 printed pages. (Year: 2011).*
HerbalLocks.com. "The Top 5 Non-Comedogenic Shampoos." http://www.herballocks.com/natural-shampoos/top-5-non-comedogenic-shampoos/, accessed by examiner on Dec. 22, 2017, 10 printed pages. (Year: 2017).*
Notification of Transmittal of the International Search Report and the Written Opinion of the International Searching Authority dated Sep. 12, 2017, in connection with corresponding international application No. PCT/US2017/036745 (12 pgs.).

(Continued)

*Primary Examiner* — Isaac Shomer
(74) *Attorney, Agent, or Firm* — Knobbe, Martens, Olson & Bear, LLP

(57) ABSTRACT

An improved hair and scalp treatment composition comprising a hair care product wherein the improvement comprises reducing the comedogenicity thereof by excluding therefrom comedogenic elements having a Fulton scale grade greater than 2.

19 Claims, No Drawings

(56) References Cited

U.S. PATENT DOCUMENTS

| | | | |
|---|---|---|---|
| 2011/0256249 A1* | 10/2011 | Campbell | A61K 8/368 424/735 |
| 2012/0082629 A1 | 4/2012 | Holger | |
| 2012/0093755 A1* | 4/2012 | Humphreys | A45D 7/06 424/70.14 |
| 2012/0189684 A1 | 7/2012 | Buckley et al. | |
| 2012/0289590 A1 | 11/2012 | Ritterman et al. | |
| 2013/0090279 A1* | 4/2013 | Hilvert | A61K 8/463 510/125 |
| 2014/0154200 A1* | 6/2014 | Lizarraga | A61Q 5/006 424/70.12 |
| 2014/0186284 A1 | 7/2014 | Sha et al. | |
| 2014/0187518 A1 | 7/2014 | Kazin et al. | |
| 2015/0139929 A1* | 5/2015 | Dixon | C11D 1/126 424/70.1 |
| 2016/0008297 A1 | 1/2016 | Schmaus et al. | |
| 2016/0206573 A1 | 7/2016 | Garcines et al. | |
| 2016/0374352 A1 | 12/2016 | Modak et al. | |
| 2017/0096418 A1* | 4/2017 | Patron | C07D 409/12 |

FOREIGN PATENT DOCUMENTS

| | | |
|---|---|---|
| EP | 2214631 B1 | 4/2013 |
| EP | 3142633 A1 | 3/2017 |
| EP | 3174519 A1 | 6/2017 |
| EP | 3191074 A1 | 7/2017 |
| EP | 2528577 B1 | 1/2018 |
| WO | 2005018629 A1 | 3/2005 |
| WO | WO 2014/134620 A1 | 9/2014 |
| WO | WO 2015/164433 A1 | 10/2015 |
| WO | WO 2015/175333 A1 | 11/2015 |
| WO | 2016012757 A1 | 1/2016 |
| WO | WO 2016/018315 A1 | 2/2016 |
| WO | WO 2016/040757 | 3/2016 |
| WO | WO 2017/034384 A1 | 3/2017 |
| WO | WO 2017/108902 A1 | 6/2017 |
| WO | WO 2018/000060 A1 | 1/2018 |

OTHER PUBLICATIONS

Kristin Collins Jackson, "3 Paraben and Sulfate Free Shampoos, Serums, and Body Washes to go Natural With This Summer", article in bustle.com (http://www.bustle.com/articles/28720-3-paraben-and-sulfate-free-shampoos-serums-and-body-washes-to-go-natural-with-this-summer), Jun. 20, 2014, 7 pgs.

Lily Talakoub, "Smooth hair—an acne-causing epidemic," Dermatology News, published Apr. 19, 2016, URL: http://www.mdedge.com/edermatologynews/article/108161/acne/smooth-hair-acne-causing-epidemic, 4 pgs.

Tina Ferraro, "Is Your Conditioner Causing You to Break Out?," TeenVogue, published Jul. 3, 2015, URL: http://www.teenvogue.com/story/hair-conditioner-causing-acne-breakouts, 4 pgs.

Valerie Tejeda, "Are Your Hair Products Making You Break Out?," TeenVogue, published Jul. 21, 2014, http://www.teenvogue.com/story/hair-products-cause-acne, 4 pgs.

Christa Joanna Lee, "How to Get Rid of Forehead Acne," TeenVogue, published Jul. 12, 2016, URL: http://www.teenvogue.com/story/how-to-get-rid-of-forehead-acne, 4 pgs.

Carly Cardellino, "13 Surprising Reasons You Keep Breaking Out," Cosmopolitan, published May 2, 2016, http://www.cosmopolitan.com/style-beauty/beauty/advice/a32686/surprising-things-that-cause-acne/, 12 pgs.

Lexy Lebsack, "The Annoying Reason You May Be Breaking Out," Refinery29, published Jan. 9, 2016, URL: http://www.refinery29.com/hair-products-skin-break-outs, 16 pgs.

Porespective, "Five Causes of Adult Acne That May Surprise You," Porespective, printed May 15, 2017, URL: https://www.porespective.com/five-causes-of-adult-acne-that-may-surprise-you/, 8 pgs.

Lauren Valenti, "The Sneaky Thing Thats Making You Break Out . . . All Over," MarieClaire, published Mar. 10, 2016, http://www.marieclaire.com/beauty/news/a19207/hair-products-skin-breakouts/, 8 pgs.

Kali Borovic, "12 Hair Mistakes That Cause Acne & Sabotage Your Best Skincare Efforts," Bustle, published Mar. 5, 2016, URL: https://www.bustle.com/articles/146009-12-hair-mistakes-that-cause-acne-sabotage-your-best-skincare-efforts, 17 pgs.

Alexis C. Perkins, et al., "Acne Vulgaris in Women: Prevalence Across the Life Span," 21 J Womens Health 223-230 (Feb. 2012), URL: http://online.liebertpub.com/toc/jwh/21/2, 9 pgs.

James Q. Del Rosso, et al., "Status Report From the American Acne & Rosacea Society on Medical Management of Acne in Adult Women, Part 1: Overview, Clinical Characteristics, and Laboratory Evaluation," 96(4) Cutis 236-241, Oct. 2015, URL: http://www.cutis.com/uploads/media/media_1b35c69_CT096010236.PDF, 6 pgs.

American Academy of Dermatology, Acne: Overview, https://www.aad.org/public/diseases/acne-and-rosacea/acne visited Jun. 6, 2016, 3 pgs.

Nancy Janiczek-Dolphin, et al., "Can sebum reduction predict acne outcome?" 163(4) Br J Dermatol 683-8, Oct. 2010, URL: http//www.medscape.com/viewarticle/730258, 10 pgs.

Emil A. Tanghetti, "The Role of Inflammation in the Pathology of Acne," 6 J Clinical and Aesthetic Dermatology, 27-35, Sep. 2013, 9 pgs.

Jamese . Fulton, Jr., "Comedogenicity and irritancy of commonly used ingredients in skin care products", j. Soc. Cosmet. Chem., 40, 321-333, Nov./Dec. 1989, 13 pgs.

\* cited by examiner

NON-COMEDOGENIC AND NON-ACNEGENIC HAIR AND SCALP CARE FORMULATIONS AND METHOD FOR USE

CROSS REFERENCE TO RELATED APPLICATION

This application claims the benefit of Provisional U.S. Patent Application No. 62/348,510, filed Jun. 10, 2016, the entire contents and disclosure of which, both express and implied, are incorporated herein by reference.

BACKGROUND

When a person uses hair products on their hair, those same hair products can migrate to the skin through various mechanisms. For example, when shampooing and/or conditioning hair, the shampoo and conditioner unavoidably come into contact with the scalp, face, neck, chest, shoulders, and back, either through direct contact or as they are rinsed off and run down the skin in the shower.

Many hair care products, including rinse off products, such as shampoos and conditioners, are also designed to leave a residue even after the product is subsequently rinsed out of the hair. Leave in haircare products by design are not rinsed out and always leave a residue. This residue may be good for the hair, but can often cause problems for the skin. This residue can be deposited on the skin directly by direct contact with the skin on the scalp, and, for example, by dripping down from the hair to the face after application as well as when it runs down the person's face, neck, chest, shoulders, and/or back in the shower. This residue can also be deposited on a person's skin indirectly, when an object successively comes into contact with the person's hair, and then their skin. For example, if the person dries their hair with a towel, the residue can be transferred to other parts of their body via the towel; residue may also be transferred from a person's hair to their face from a pillowcase.

Most hair care products are developed without consideration of the impact that the product will have on the user's skin, despite the fact that contact with the skin with each use is unavoidable. Many hair care products can also build up on the skin or scalp over time, particularly if the hair care product is intended to be left in for days at a time; as a result, the hair care products may have a dramatically detrimental effect on the skin of a user. Many hair care products also contain ingredients that can trigger irritation of the skin in some users. In some cases, hair and skin treatments may also have incompatible regimens; for example, a person with parched hair strands resulting from coloration of their hair, may require hair products with significant amounts of oils and conditioning agents, some of which can be comedogenic to the skin.

According to the American Academy of Dermatology [AAD], a "comedo" is an "acne lesion", a hard blockage created from an excess of sebum combined with keratin (skin debris) in a pore which can lead to whiteheads, blackheads and pimples. Accordingly, the term, "comedogenic", refers to ingredients or products that have a tendency to block pores and promote comedones or acne.

Those with curly and/or frizzy hair may use smoothing products that traditionally contain ingredients such as oils and conditioning agents that can be comedogenic, or can become comedogenic in combination with other ingredients. For example, some common hair smoothing products, such as some silicone hair smoothing products, have not been found to be significantly comedogenic on their own, but have been found to increase the penetration of other ingredients in a formulation, which may result in a more comedogenic product. This means that hair care products can, in many cases, contribute to and exacerbate skin conditions such as acne (or "acne vulgaris"), the most common skin disease in the United States.

Acne vulgaris affects up to 50 million people in the United States alone. Acne is not just a condition that affects teenagers. Acne is highly prevalent in adult women, with one study showing that 45% of women aged 21-30, 26% aged 31-40, and 12% aged 41-50 had clinical acne. Adult acne in women is also on the rise. According to the American Academy of Dermatology (AAD), acne can contribute to depression, anxiety, and poor self-image. It can also leave permanent scars.

Acne may arise when hair follicles (pilosebaceous units) become clogged. Acne is characterized by comedones, clogged pores in the skin, which can either be open comedones ("blackheads") or closed comedones ("whiteheads"). Acne is also characterized by pimples, which can appear as inflammatory papules or pustules, cysts, or nodules.

Acne is caused by several major mechanisms: inflammation, oil/sebum, follicular hyperkeratinization, *propionibacterum acnes* (*p. acnes*), a bacteria, and hormones. Sebum, an oily substance secreted by the sebaceous glands of the skin, can cause dead skin cells to stick together, which can clog pores and plug hair follicles, causing acne. Sebum secretion has been correlated with acne severity, with high sebum secretion levels tended to be correlated with more severe acne; in some cases, a high sebum secretion rate may even be the decisive factor in inflammatory acne.

*P. acnes* is a bacteria that lives on the skin and can also get inside the follicle and contribute to inflammation, causing inflammatory acne lesions, including papules, cysts, and nodules. Conventional belief was that all inflammatory acne lesions arose from comedones. Recently, acne has been identified to be a primary inflammatory condition. There is evidence that inflammation plays a role at all stages of acne development, and can even be observed subclincally before the formation of comedones.

Acne can also be caused or exacerbated by certain cosmetics or styling products. "Acne cosmetica" is a form of acne that is caused by or exacerbated by the use of certain cosmetic products, including, though not limited to, makeup and sunscreen. "Acne cosmetica" typically results from a chemically-induced plugging of the hair follicles by these products. Certain cosmetic products can also produce folliculitis, or inflammation of the hair follicle, which appears as small bumps on the skin that can be skin-colored, pink, or red, having an appearance similar to acne.

For example, "pomade acne" is a similar condition to "acne cosmetica," also resulting from chemically-induced plugging of the hair follicles, and characterized by bumps on the forehead caused by oily hair care styling products. This condition was originally described primarily in African American men. Both "acne cosmetica" and "pomade acne" may also be referred to generally as "acneiform eruptions." Pomade acne has more recently been described as being an issue in all skin types, in both men and women due to hair products that smooth the hair, add shine, and reduce frizz. These products can contain oils, and waxes that clog pores, trap bacteria, and cause inflammation. Users of these products may find that these products are transferred to their pillow at night if left in their hair; as a result, users of these products may find that their faces are rolling around in oily, waxy, hair products all night. (Other hair products, particularly products not designed to be washed out within a day or so, may also cause similar problems.)

The ingredients in these hair products that clog pores and cause acne are not limited to oils and waxes used for styling and conditioning, as other ingredients can be problematic. Comedogenic or potentially comedogenic components include PVP/DMAPA acrylates, cyclopentasiloxane, panthenol, dimethicone, some silicones (typically to a mild degree), Quaternium-70, oils, and petrolatum. These ingredients may be comedogenic themselves, or, as mentioned previously, may enhance the comedogenicity, irritation, and/or allergic potential of other ingredients. For example, petrolatum itself is non-comedogenic, but is occlusive and can trap moisture and other ingredients in the hair follicles, causing stronger reactions to these ingredients.

For patients with adult acne, the AAD recommends using personal care products, including hair care products, which have one of the following labels: "non-comedogenic," "non-acnegenic," "oil-free," or "won't clog pores." However, these labels are not typically found on hair care products because hair care products are not typically formulated to be "non-comedogenic," "non-acnegenic," or "oil-free." Currently, it is not standard to test hair care products for comedogenicity or acnegenicity, or to have oil-free hair care products for acne-prone skin. In fact, there is a trend in the beauty industry to add oils to hair care products.

Many common hair care products, such as shampoos, conditioners, and other hair care products, contain oils that are or have the potential to be comedogenic. As mentioned, other products, such as silicones, can also be comedogenic in combination with other products in a formulation. Many leave-in products also contain significant quantities of these oils and silicones that can be comedogenic, including, though not limited to, styling creams, gels, pomades, hairsprays, smoothing serums, heat styling sprays, anti-frizz serums, heat-protectants, and shine sprays. Other materials in hair care products are also potentially comedogenic.

A list of comedogenic or potentially comedogenic materials includes, but is not limited to, acetylated lanolin, acetylated lanolin alcohol, algin, almond oil, apricot kernel oil, avocado oil, grapeseed oil, bismuth oxychloride. butyl stearate, carrageenan, ceteareth 20. cetyl acetate. cocoa butter, coconut oil, coal tar, hydrogenated oils, D & C Red #17, D & C Red #21, D & C Red #3, D & C Red #30. D & C Red #36, decyl oleate, disodium oleamido peg-2 sulfosuccinate, lanolin, lanolin derivatives, ethylhexyl palmitate, glyceryl stearate SE, glyceryl-3-diisostearate, hexadecyl alcohol, hydrogenated vegetable oil, isocetyl alcohol, isocetyl stearate, isodecyl oleate, isopropyl isostearate, isopropyl myristate, isopropyl palmitate, isostearyl isostearate, isostearyl neopentanoate, laureth-23, laureth-4, lauric acid, mink oil, myristic acid, myristyl lactate, myristyl myristate, octyl palmitate, octyl stearate, oleic acid, oleates, oleth-3, oleyl alcohol, olive oil, peg 200 dilaurate, PEG 8 stearate, PG monostearate, PPG 2 myristyl propionate, polyglyceryl-3-diisostearate, propylene glycol monostearate, sesame oil, sodium laureth sulfate, sodium lauryl sulfate, sorbitan oleate, soybean oil, steareth 10, stearyl heptanoate, sulfated oils, triethanolamine, wheat germ glyceride, wheat germ oil, and certain conditioning agents. Occlusive agents, including some of the above materials, can often contribute to comedogenicity and acne. See Fulton, *J. Soc. Cosmet. Chem.*, 40, 321-333 (November/December 1989) "Comedogenicity and irritancy of commonly used ingredients in skin care products" for a discussion of comedogenic materials.

In addition, most shampoos contain potentially irritating surfactants, such as sulfate-based surfactants; for example, sodium lauryl sulfate and ammonium lauryl sulfate are common surfactants that can cause irritation. Irritation to the skin can produce folliculitis and small papules on the skin, which may appear similar to acne. The folliculitis that occurs is indistinguishable from acne to the majority of hair care product users. Irritation of the follicle can also increase penetration of other materials in the hair care product into the skin follicles, increasing the potential comedogenicity and acnegenicity of many materials that could come into contact with the skin, including other materials in the hair care product formulation.

SUMMARY

Non-comedogenic and/or non-acnegenic hair care formulations may be disclosed. In some embodiments, the hair care formulation may be any kind of hair care product, including, for example, a shampoo, conditioner, or a styling product such as a styling spray, a hair spray, a shine enhancer, a root spray, a hair masque, a gel, or a styling cream, or some combination thereof. Such a formulation may allow for the cleaning, conditioning, and/or styling of the hair of a user without causing or promoting irritation or acne on the skin of the user. Such a formulation may also help resolve skin irritation, breakouts, and/or acne.

In an exemplary embodiment, the formulation may be used as part of a two-step method for washing hair. In the first step, a non-comedogenic and/or non-acnegenic shampoo is applied to cleanse the hair, and, in the second step, a non-comedogenic and/or non-acnegenic hair conditioner may be applied.

DETAILED DESCRIPTION OF THE EMBODIMENTS

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

According to an exemplary embodiment, certain hair care formulations that are non-comedogenic, or which are non-comedogenic and which do not tend to cause acne (non-acnegenic), may be disclosed. In some exemplary embodiments, such hair care formulations may prevent, improve, and/or alleviate acne, acneiform eruptions, folliculitis, pimples, blemishes, and/or skin breakouts.

According to another exemplary embodiment, methods for using the hair care formulations may be described. Such methods may be used in isolation or as part of a regimen, as may be desired. For example, in an exemplary embodiment, hair care formulations may be used in a multi-step shower method. This method may include, in step 1, applying shampoo; and, in step 2, applying conditioner. In some exemplary embodiments, hair care products may be used as part of a method for using a hair care formulation, or may be used independently, as desired. These products, or other products (such as shampoo, conditioner, and styling product) may be sold as part of a kit and designed to be compatible with or to complement one another, as may be desired.

As mentioned, a variety of causes for acne can exist, including follicular hyperkeratinization (keratinocytes stick together and block the pore), inflammation, sebum, *propionibacterium acnes*, hormones, and other factors. Therefore, an exemplary embodiment of a non-comedogenic or non-acnegenic hair care product may include a keratinolytic agent, an anti-inflammatory agent, a sebum modulator, and/or antimicrobial agents, as well as other ingredients or additives, as desired. In some exemplary formulations, only one or more of the above components may be added; for example, in an exemplary embodiment, an anti-inflammatory agent may be added, but a keratinolytic agent, sebum modulator, or antimicrobial agent may not be added. Other combinations may also be envisioned, as desired.

According to an exemplary embodiment, a keratinolytic agent may be added to the composition, and may, for example, be used to modulate and correct abnormal follicular keratinization. This may help to prevent obstruction of the hair follicle and subsequent bacterial overgrowth. Exemplary keratinolytic agents that may be used in the formulation include willowbark (salicin) or bakuchiol. In other exemplary embodiments, as discussed above, a keratinolytic agent may not be present.

According to an exemplary embodiment, an anti-inflammatory agent may be added to the composition and may, for example, be used to reduce skin inflammation, therefore preventing and/or improving acne lesions, including comedones, papules, cysts, and nodules. Exemplary anti-inflammatory agents that may be used in the formulation include bisabolol (an anti-inflammatory chamomile derivative), stearyl glycyrrhetinate, or grapefruit seed extract (*Citrus Grandis* seed extract). Exemplary anti-irritant agents that may be used in the formulation include pea protein.

According to an exemplary embodiment, a sebum modulator may be added to the composition and may, for example, be used to control the amount of sebum secreted by the sebaceous glands of the skin. Clinically, measures to decrease sebum have been shown to improve acne. For example, both systemic and topical treatments may be available. An exemplary embodiment of a formulation may make use of one or more topical sebum modulators, as desired. Systemic retinoids, including isotretinoin, reduce sebum, and are one of the most powerful acne treatments available, but generally must be administered orally; as such, an exemplary embodiment of a formulation may be formulated to be compatible with a simultaneous systemic retinoid treatment or other oral or topical acne treatment of a patient, if desired. Exemplary sebum modulators that may be used in the formulation include Farnesyl Acetate, Panthenyl Triacetate, Tocopheryl Acetate, or grapefruit seed extract (*Citrus Grandis* seed extract). In other exemplary embodiments, as discussed above, a sebum modulator may not be present. An exemplary embodiment of a formulation may also be formulated to be compatible with a separate topical acne treatment regimen, if desired.

According to an exemplary embodiment, other ingredients or additives may be added to the formulation. These may serve a variety of purposes, or may serve multiple purposes. For example, exemplary additives may be added for the purpose of protecting against pollution or protecting against ultraviolet light (UV), or for other purposes, as may be desired. Exemplary multifunction additives that may be added to the formulation include algae extract, juice pressed from blackcurrant and raspberry leaves, butyl avocadate, zinc PCA, epilobium fleischeri extract, *Laminaria Cloustoni* extract, grapefruit seed extract (*Citrus Grandis* seed extract), or *Moringa oleifera* seed extract (horse-radish tree). However, in other exemplary embodiments, no multifunction additives may be added to the formulation, as may be desired.

According to an exemplary embodiment, if desired, one or more high molecular weight ingredients may be added to the formulation. For example, according to an exemplary embodiment, a large constituent such as a polymer of polyethylene glycol (PEG) may be added to the formulation. This may serve to reduce the comedogenicity of the overall formulation.

According to an exemplary embodiment, if desired, one or more of a polar sugar or a heavy metal may be added to the formulation to reduce the comedogenicity of the overall formulation. For example, according to an exemplary embodiment, zinc may be added to the formulation.

According to an exemplary embodiment, the degree of etholxylation of one or more of the molecules used in the formulation may be increased, or one or more ethoxylated materials may be added.

According to an exemplary embodiment, ingredients which are known to be comedogenic or which are potentially comedogenic, may be excluded from the formulation. For example, in an exemplary embodiment, the formulation may be oil-free, and free of laureth-4, isopropyl myristate and its analogs, lanolins, waxes, and certain conditioning agents, as well as other comedogenic or acnegenic compounds or compositions listed above or in a previous section. Occlusive agents, such as some of the above materials, can often contribute to comedogenicity and acne. In an embodiment, ingredients which are known to be irritating or potentially irritating, or ingredients that function as common allergens or which are not known to be hypoallergenic, may also be excluded from the formulation. For example, according to an exemplary embodiment, the formulation may be sulfate-free. In some embodiments, ingredients that can exacerbate the comedogenic or acnegenic properties of another ingredient but which do not themselves have significant comedogenic or acnegenic properties, such as silicone, may also be excluded. For example, in some exemplary embodiments, a silicone substitute, such as hemisqualane (a non comedogenic silicone substitute that has skin benefits) may be substituted for silicone in some quantity. In some other exemplary embodiments, silicone or another ingredient that can exacerbate the comedogenic or acnegenic effects of another ingredient may be included, and the comedogenic and acnegenic properties of the formulation may be controlled by controlling other ingredients of the formulation instead.

In an exemplary embodiment, ingredients which are known to be comedogenic or which are known to potentially be comedogenic when present in a formulation at a particular level may be kept below the level at which they are comedogenic. For example, according to an exemplary embodiment, a non-comedogenic conditioner may be provided by reducing but not eliminating the quantity of cetearyl alcohol present in a formulation; cetearyl alcohol may be comedogenic in high concentrations and minimally reactive at low concentrations.

In some embodiments, the products will also be paraben-free, formaldehyde-free, and phthalate-free, or may not have any of those components in any significant quantities.

Generally, those ingredients with a Fulton scale grade [Fulton, *J. Soc. Cosmet. Chem.*, 40, 321-333 (November/December 1989) "Comedogenicity and irritancy of commonly used ingredients in skin care products"] of greater than about 2 may be excluded from the compositions of the invention.

In an exemplary embodiment, the pH of the formulation may be controlled at a desirable level, which may serve to reduce irritation and inflammation. It may be understood that the skin of a typical person is slightly acidic, typically having a pH of around 5.5 to 6.5, whereas many soaps, particularly bar soaps, may be formulated to have a pH that is slightly basic (around 8 to 9). This may cause skin irritation and inflammation. According to an exemplary embodiment, one or more acids may be added to the formulation such that the formulation has a pH that is neutral or slightly acidic, as desired. In some exemplary embodiments, different optimal ranges may be targeted for different non-comedogenic and/or non-acnegenic hair care formulations; for example, in an exemplary embodiment, the optimal pH of the shampoo may be 5.5-6.5 and the optimal pH of the conditioner may be 4.8-5.3. In other exemplary embodiments, pH may be controlled at another level, if desired; in other exemplary embodiments, no additives may be added to the composition in order to control pH.

In another exemplary embodiment, the composition may also be formulated to have desirable qualities as a hair care product. For example, according to an exemplary embodiment, the composition may be rinseable and designed to leave only skin-friendly residue when rinsed. This may further minimize the potential for irritation or comedogenicity from the product. The rinseability of the product may also provide other benefits, such as other benefits to the skin, such as may be desired. In another exemplary embodiment, the composition may be formulated to be color-safe or may otherwise be formulated to have minimal impact on color-treated hair.

According to an exemplary embodiment, variations of the composition may be formulated for use in specialized hair care products. In an exemplary embodiment, stratification between said hair care products may be based on hair type, benefit, or intended customer. For example, according to an exemplary embodiment, variations of an exemplary composition may be prepared specifically for and marketed at women, men, teens, and others. In an exemplary embodiment, variations of an exemplary composition may be prepared specifically for curly hair, damaged hair, dry hair, fine or flat hair, as well as more typical or normal hair. In an exemplary embodiment, variations of an exemplary composition may be prepared specifically for anti-frizzing, for promoting shine, for smoothing hair, for strengthening hair, or for any other purposes as may be desired.

An exemplary formulation of a hair care product formulated to have non-comedogenic and/or non-acnegenic properties may be disclosed in table 1 and may be made by combining the following components in the proportions stated below. In an exemplary embodiment, the hair care product in table 1 may be used as a shampoo.

TABLE 1

Non-Comedogenic/Acnegenic Shampoo Exemplary Compositions

| | Ingredient | Broad % | Preferred % |
|---|---|---|---|
| Part A | Water | 10.0-70.0 | 20.0-40.0 |
| | Disodium EDTA | 0.00-1.00 | 0.01-0.20 |
| Part B | Glycerin | 0.00-10.0 | 0.01-3.00 |
| | Guar Hydroxypropyltrimonium chloride | 0.05-5.00 | 0.01-0.50 |
| Part C | Citric acid | 0.00-2.00 | 0.01-1.00 |
| Part D | Phenoxyethanol | 0.01-1.00 | 0.01-1.00 |
| | Ethylhexylglycerin | 0.01-1.00 | 0.01-0.50 |
| | Polyquaternium-7 | 0.50-10.0 | 0.50-5.00 |
| | Sodium lauroyl methyl isethionate | 10.0-70.0 | 30.0-60.0 |
| | Cocamidopropylamine oxide | 1.00-20.0 | 5.00-10.0 |
| | Glycol distearate | 0.00-10.0 | 0.50-1.00 |
| Part E | Water | 0.00-8.00 | 2.00-8.00 |
| | Acrylates copolymer | 1.00-15.0 | 2.00-6.00 |
| Part F | C13-C15 alkane | 0.01-10.0 | 0.01-1.50 |
| | Bisabolol | 0.01-1.00 | 0.01-0.50 |
| | Fragrance | 0.00-3.00 | 0.01-1.00 |
| | Aminomethyl propanol | 0.01-5.00 | 0.01-1.00 |

In exemplary embodiments, the components of a chemical composition provided under a trade name may be used instead of the composition provided under the trade name. For example, according to an exemplary embodiment, an exemplary formulation of hair care product may include phenoxyethanol and ethylhexylglycerin as separate components rather than including Euxyl PE 9010. This may allow the component chemicals (such as, again, phenoxyethanol and ethylhexylglycerin) to be provided in different proportions than are found in the chemical composition provided under the trade name. The acrylates copolymer listed in table 1 may be that sold under the trade name, Carbopol Aqua SF-1; however, it will be understood by those skilled in the art that any suitable lightly cross-linked rheology modifying acrylate copolymer may be employed in the practice of the invention.

According to an exemplary embodiment, an exemplary hair care product formulation of table 1 may be prepared according to the following process or a process similar to the following. In a first step, a sanitized mixing vessel may be prepared, and a quantity of deionized water may be added to the sanitized mixing vessel. The remaining components of Part A, which in the exemplary case shown in table 2 may be Disodium EDTA, may then be mixed into the mixing vessel.

In a next step, the ingredients of part B may be premixed and may then be added to the batch. The ingredients may be mixed into the batch until the batch is uniform. The ingredients of part C may then be added to the combined batch, and again mixed until the resulting batch is completely smooth.

The combined parts A, B, and C may then be heated. For example, according to an exemplary embodiment, the combined batch may be heated to a temperature within a range of 60 to 65° C.

The ingredients of Part D may then be added. The resulting batch may be mixed until all solids are melted and the batch is uniform. Once the batch has been fully mixed, the batch may be cooled to a temperature within a range of 40 to 45° C.

Once the batch has been cooled to a temperature within a range of 40 to 45° C., the parts of part E may be added. The components of part E may be pre-mixed prior to addition, which may be done, for example, concurrently with another step preceding the addition of components in part E. Once the parts of part E have been added, the resulting batch may be mixed until uniform.

Once the resulting batch has been mixed until uniform, the ingredients of part F may be added, and likewise mixed until uniform. The batch may then be cooled to a temperature of approximately 35° C. According to an exemplary embodiment, the pH of the batch may at this time be adjusted to a pH within a range of 6.50 to 6.75.

The resulting composition may be a hair care product having the appearance of semi-viscous pearlized gel. The color may be pearlescent white to off-white, which may in some exemplary embodiments be adjusted if desired. The odor may be characteristic of the fragrance added to the composition; in some exemplary embodiments, the fragrance may be reduced or left out of the composition in order to produce an odorless composition. In an exemplary embodiment, the composition may have a pH at 25° C. of between 6.5 and 7.0, a viscosity at 25° C. (RVT), at spindle 5 at 20 rpm, of between 1000 and 12,000 cPs, and a specific gravity at 25° C. of between 0.98 and 1.03. In an exemplary embodiment, the composition may be kept to a low level of viable bacterial or fungal cells or other colony-forming units (CFU), of approximately <10 CFU/g; the composition may also be kept free of pathogens.

According to an exemplary embodiment, in a production environment, one or more small-scale batches, such as lab or pilot batches, may be made prior to large-scale manufacturing. Adjustments may be made to the production process based on, for example, the results of a batch made in a particular production environment.

Another exemplary formulation of a hair care product formulated to have non-comedogenic and/or non-acnegenic properties may be disclosed in table 2 and may be made by combining the following components in the proportions stated below. In an exemplary embodiment, the hair care product in table 2 may be used as a hair conditioner.

TABLE 2

Non-Comedogenic/Acnegenic Hair Conditioner Exemplary Compositions

| | Ingredient | Broad % | Preferred % |
|---|---|---|---|
| Part A | Water | 50.0-90.0 | 60.0-90.0 |
| | Disodium EDTA | 0.00-1.00 | 0.01-0.10 |
| | Phenoxyethanol | 0.10-5.00 | 0.75-1.25 |
| | Ethylhexylglycerin | 0.10-2.00 | 0.10-0.50 |
| | Citric acid | 0.01-1.00 | 0.01-0.50 |
| | Stearamidopropyl dimethylamine | 1.00-10.0 | 1.00-2.50 |
| | Polysorbate 80 | 0.00-5.00 | 0.10-0.10 |
| Part B | Cetearyl alcohol | 0.50-10.0 | 1.00-5.00 |
| | Behentrimonium chloride | 0.10-5.00 | 0.50-3.00 |
| | Cetyl palmitate | 0.50-5.00 | 1.00-4.00 |
| | C13-C15 alkane | 0.50-15.0 | 2.00-7.00 |
| | Shea butter cetyl esters | 0.10-8.00 | 0.50-2.00 |
| Part C | Glycerin | 0.00-10.0 | 0.10-2.00 |
| | Bisabolol | 0.01-1.00 | 0.01-0.50 |
| | Fragrance | 0.00-5.00 | 0.50-2.00 |

According to an exemplary embodiment, an exemplary hair care product formulation of table 2 may be prepared according to the following process or a process similar to the following. In a first step, a sanitized mixing vessel may be prepared, and a quantity of deionized water may be added to the sanitized mixing vessel. This DI water may then be heated to a temperature within the ranges of 80 to 85° C.

The remaining components of Part A may then be mixed into the mixing vessel. According to an exemplary embodiment, the remaining components of Part A may be added in an order or sequence, which may for example be the order in which they are shown in the table. In an exemplary embodiment, the ingredients may be added only once the previous ingredient has been fully dissolved. For example, in an exemplary embodiment, the phenoxyethanol of part A may be added, mixed until fully dissolved, and only then will the ethylhexylglycerin of part B be added.

The components of part B may be combined in a separate mixing vessel. According to an exemplary embodiment, the components of part B may be heated to a temperature in the range of 80 to 85° C. after combination, and may then be mixed until uniform.

The components of part B may then be combined with the components of part A, for example by adding the components of part B to the mixing vessel of part A. The resulting batch may then be mixed until it is smooth and uniform. The batch may then be cooled to a temperature within the range of 35 to 40° C.; according to an exemplary embodiment, mixing may be continued during this cooling process.

The ingredients of part C may then be added to the combined batch of parts A and B. According to an exemplary embodiment, ingredients may be added alone or in combination, as may be desired. The resulting batch may be mixed until uniform; following this, it may continue to be mixed and may be cooled (for example by ambient temperature) until the temperature of the batch reaches a temperature between 30 and 35° C.

The resulting composition may be a hair care product having the appearance of viscous cream. The color may be white to off-white, which may in some exemplary embodiments be adjusted if desired. The odor may be characteristic of the fragrance added to the composition; in some exemplary embodiments, the fragrance may be reduced or left out of the composition in order to produce an odorless composition. In an exemplary embodiment, the composition may have a pH at 25° C. of between 3.8 and 5.5 a viscosity at 25° C. (RVT), at spindle 5 at 20 rpm, of between 2000 and 30,000 cPs, and a specific gravity at 25° C. of between 0.98 and 1.03. In an exemplary embodiment, the composition may be kept to a low level of viable bacterial or fungal cells or other colony-forming units (CFU), of approximately <10 CFU/g; the composition may also be kept free of pathogens.

Another exemplary formulation of a hair care product formulated to have non-comedogenic and/or non-acnegenic properties may be disclosed in table 3 and may be made by combining the following components in the proportions stated below. In an exemplary embodiment, the hair care product in table 3 may be used as a curly styling cream.

TABLE 3

Non-Comedogenic/Acnegenic Curly Styling Cream Exemplary Compositions

| | Ingredient | Broad % | Preferred % |
|---|---|---|---|
| Part A | Water | 50.0-90.0 | 75.0-85.0 |
| | Disodium EDTA | 0.00-1.00 | 0.05-0.20 |
| | Phenoxyethanol | 0.10-5.00 | 0.75-1.25 |
| | Ethylhexylglycerin | 0.10-2.00 | 0.10-0.50 |
| | Citric acid | 0.01-1.00 | 0.01-0.50 |
| | Stearamidopropyl dimethylamine | 1.00-10.0 | 1.00-2.50 |
| | Polysorbate 80 | 0.00-5.00 | 0.10-1.00 |
| Part B | Cetearyl alcohol | 0.50-10.0 | 1.00-5.00 |
| | Behentrimonium chloride | 0.10-5.00 | 0.50-3.00 |
| | Squalene | 0.00-8.00 | 0.50-5.00 |
| | C13-C15 alkane | 0.50-15.0 | 1.00-5.00 |
| | Shea butter cetyl esters | 0.10-8.00 | 0.50-5.00 |

TABLE 3-continued

Non-Comedogenic/Acnegenic Curly Styling Cream Exemplary Compositions

| | Ingredient | Broad % | Preferred % |
|---|---|---|---|
| Part C | Polyimide-1 | 0.00-3.00 | 0.10-1.00 |
| Part D | Puricare ™ LS9727* | 0.00-8.00 | 1.00-3.00 |
| | Bisabolol | 0.01-1.00 | 0.01-1.00 |
| | Hydrolyzed Pea Protein | 0.00-8.00 | 0.50-2.00 |
| | Keratrix ™** | 0.00-10.0 | 1.50-4.50 |
| | Fragrance | 0.00-5.00 | 0.01-2.00 |

*Includes water, glycerin, moringa Oleifera seed extract
**Includes water, glycerin, hydrolyzed ceratonia siliqua seed extract, zea mays starch, guar hydroxypropyltrimonium chloride, polyquaternium-7

According to an exemplary embodiment, an exemplary hair care product formulation of table 3 may be prepared according to the following process or a process similar to the following. In a sanitized mixing vessel, add disodium EDTA and water from Part A. Begin heating to 75-80° C. while mixing. Add remaining ingredients of Part A. Mix with heat until clear and all solids are dissolved. In a separate vessel, combine ingredients in Part B. Heat Part B to 75-80° C. and mix until uniform. Add Part B to Part A and mix until smooth and uniform. Add Part C to batch, mix until uniform and cool to 35-40° C. Add ingredients in Part D and mix until uniform. Continue mixing batch until temperate reaches 30-35° C. The product has the appearance of a white viscous cream with a pH@ 25° C.: 3.8-4.2; viscosity @ 25° C. (RVT): Spindle 5, 20 RPM 4,000-8,000 cPs; specific gravity @ 25° C.: 0.98-1.03; microbiology <10 CFU/g, No pathogens Another exemplary formulation of a hair care product formulated to have non-comedogenic and/or non-acnegenic properties may be disclosed in table 4 and may be made by combining the following components in the proportions stated below. In an exemplary embodiment, the hair care product in table 4 may be used as a blow dry styling cream.

TABLE 4

Non-Comedogenic/Acnegenic Blow Dry Styling Cream Exemplary Compositions

| | Ingredient | Broad % | Preferred % |
|---|---|---|---|
| Part A | Water | 50.0-90.0 | 75.0-85.0 |
| | Disodium EDTA | 0.00-1.00 | 0.05-0.20 |
| | Phenoxyethanol | 0.10-5.00 | 0.75-1.25 |
| | Ethylhexylglycerin | 0.10-2.00 | 0.10-0.50 |
| | Citric acid | 0.01-1.00 | 0.01-0.50 |
| | Stearamidopropyl dimethylamine | 1.00-10.0 | 1.00-2.50 |
| | Polysorbate 80 | 0.00-5.00 | 0.10-1.00 |
| Part B | Cetearyl alcohol | 1.00-5.00 | 1.00-5.00 |
| | Behentrimonium chloride | 0.50-3.00 | 0.50-3.00 |
| | Squalene | 0.50-5.00 | 0.50-5.00 |
| | C13-C15 alkane | 1.00-5.00 | 1.00-5.00 |
| | Shea butter cetyl esters | 0.50-5.00 | 0.50-5.00 |
| Part C | Puricare ™ LS9727 | 0.00-8.00 | 1.00-3.00 |
| | Bisabolol | 0.01-1.00 | 0.01-1.00 |
| | Hydrolyzed Pea Protein | 0.00-8.00 | 0.50-2.00 |
| | Keratrix ™ | 0.00-10.0 | 1.50-4.50 |
| | Fragrance | 0.00-5.00 | 0.01-2.00 |

According to an exemplary embodiment, an exemplary hair care product formulation of table 4 may be prepared according to the following process or a process similar to the following. In a sanitized mixing vessel, add disodium EDTA and water from Part A. Begin heating to 75-80° C. while mixing. Add remaining ingredients of Part A. Mix with heat until clear and all solids are dissolved. In a separate vessel, combine ingredients in Part B. Heat Part B to 75-80° C. and mix until uniform. Add Part B to Part A and mix until smooth and uniform. Continue mixing and cool to 35-40° C. Add ingredients in Part C and mix until uniform. Continue mixing batch until temperate reaches 30-35° C. The product has the appearance of a white viscous cream with a pH@ 25° C.: 3.8-4.2; viscosity @ 25° C. (RVT): Spindle 5, 20 RPM 3,000-8,000 cPs; specific gravity @ 25° C.: 0.98-1.03; microbiology <10 CFU/g, No pathogens According to an exemplary embodiment, in a production environment, one or more small-scale batches, such as lab or pilot batches, may be made prior to large-scale manufacturing. Adjustments may be made to the production process based on, for example, the results of a batch made in a particular production environment.

Alternative compositions may also be envisioned, for example for other compositions of shampoos or conditioners or for other types of hair care products, such as styling gels or even combined shampoos and conditioners. For example, some embodiments may have relative compositions different from those shown; an exemplary composition may have a higher weight percent of one component chemical and a lower weight percent of a second component chemical. Equivalent or substantially equivalent component chemicals may also be substituted for chemicals within a composition. Appropriate substitutions may be appreciated by one of skill in the art.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A non-comedogenic hair and scalp treatment composition
    formulated as a hair shampoo, wherein the composition comprises:
    water, wherein the water is present in an amount between 10.0 and 70.0%,
    guar hydroxypropyltrimonium chloride, wherein the guar hydroxypropyltrimonium chloride is present in an amount between 0.05 and 5.00%,
    phenoxyethanol, wherein the phenoxyethanol is present in an amount between 0.01 and 1.00%,
    ethylhexylglycerin, wherein the ethylhexylglycerin is present in an amount between 0.01 and 1.00%,
    sodium lauroyl methyl isethionate, wherein the sodium lauroyl methyl isethionate is present in an amount between 10.0 and 70%,
    cocamidopropylamine oxide, wherein the cocamidopropylamine oxide is present in an amount between 1.00 and 20.0%,
    acrylate copolymer, wherein the acrylate copolymer is present in an amount between 1.00 and 15.0%,
    C13-C15 alkanes, wherein the C13-C15 alkanes are present in an amount between 0.01 and 10.0%,
    bisabolol, wherein the bisabolol is present in an amount between 0.01-1.00%
    aminomethyl propanol, wherein the aminomethyl propanol is present in an amount between 0.01 and 5.00%, wherein the composition excludes comedogenic elements having a Fulton scale grade greater than 2.

2. The composition of claim 1 wherein the composition excludes irritant elements having a Fulton scale grade greater than 2.

3. The composition of claim 1, excluding oils, parabens, and sulfates.

4. The composition of claim 1, further comprising an element selected from the group consisting of an anti-inflammatory agent, an anti-irritant agent, an anti-microbial agent, a sebum modulator, a keratinolytic agent and mixtures thereof.

5. The composition of claim 1, additionally comprising at least one of: disodium EDTA, glycerin, citric acid, glycol distearate, and fragrance.

6. The composition of claim 1, further comprising
disodium EDTA, wherein the disodium EDTA is present in an amount between 0.01 to 1.00%,
glycerin, wherein the glycerin is present in an amount ranging between 0.01 and 10. 0%,
citric acid, wherein the citric acid is present in an amount ranging between 0.01 and 2.00%,
glycerol distearate, wherein the glycerol distearate is present in an amount between 0.10 and 10.0%
fragrance, wherein the fragrance in present in an amount ranging between 0.01 and 3.00%.

7. The composition of claim 1 formulated as a clarifying shampoo.

8. The composition of claim 1 formulated as a dry shampoo.

9. The composition of claim 1 formulated for application to men's hair.

10. The composition of claim 1 formulated for application to women's hair.

11. The composition of claim 1 formulated for application to a teenager's hair.

12. The composition of claim 1 formulated for application to pre-adolescent children's hair.

13. A kit comprising a packaged composition of claim 1, and instructions for use.

14. A method for cleansing hair comprising applying the composition of claim 1 thereto.

15. A non-comedogenic hair and scalp treatment composition formulated as a hair conditioner, the composition comprising:
water, wherein the water is present in an amount between 50.0 and 90.0%,
phenoxyethanol, wherein the phenoxyethanol is present in an amount between 0.10 and 5.00%,
citric acid, wherein the citric acid is present in an amount between 0.01 and 1.00%,
stearamidopropyl dimethylamine, wherein the stearamidopropyl dimethylamine is present in an amount between 1.00 and 10.0%,
cetearyl alcohol, wherein the cetearyl alcohol is present in an amount between 0.50 and 10.0%,
benhentrimonium chloride, wherein the benhentrimonium chloride is present in an amount between 0.1 and 5.00%,
cetyl palmitate, wherein the cetyl palmitate is present in an amount between 0.50 and 5.00%,
C13-C15 alkanes, wherein the C13-C15 alkanes are present in an amount between 0.50 and 15.0%,
shea butter cetyl esters, wherein the shea butter cetyl esters are present in an amount between 0.10 and 8.00%,
bisabolol wherein the bisabolol is present in an amount between 0.01 and 1.00%,
wherein the composition excludes comedogenic elements having a Fulton scale grade greater than 2.

16. The composition of claim 15, additionally comprising at least one of: disodium EDTA, polysorbate 80, glycerin, and fragrance.

17. The composition of claim 15, additionally comprising:
disodium EDTA, wherein the disodium EDTA is present in an amount between 0.01 and 1.00%,
polysorbate 80, wherein the polysorbate 80 is present in an amount between 0.10 and 5.00%,
glycerin, wherein the glycerin is present in an amount between 0.01 and 10.0%,
fragrance, wherein the fragrance is present in an amount between 0.01 and 5.00%.

18. The composition of claim 15 formulated as a deep hair conditioner.

19. A method for conditioning hair comprising applying the composition of claim 15 thereto.

* * * * *

UNITED STATES PATENT AND TRADEMARK OFFICE
CERTIFICATE OF CORRECTION

PATENT NO. : 9,949,915 B2  
APPLICATION NO. : 15/618420  
DATED : April 24, 2018  
INVENTOR(S) : Iris Rubin et al.

Page 1 of 1

It is certified that error appears in the above-identified patent and that said Letters Patent is hereby corrected as shown below:

In the Specification

In Column 2, Lines 24-25: change "propionibacterum" to --propionibacterium--.

In Column 2, Line 40: change "subclincally" to --subclinically--.

In Column 3, Line 41: change "oxychloride." to --oxychloride,--.

In Column 3, Line 42: change "20." to --20,--.

In Column 3, Line 42: change "acetate." to --acetate,--.

In Column 3, Line 44: change "#30." to --#30,--.

In Column 6, Line 25: change "etholxylation" to --ethoxylation--.

In Column 11, Line 31: after "pathogens" insert --.--.

In Column 12, Line 9: after "pathogens" insert --.--.

In the Claims

In Column 13, Line 25: In Claim 6, change "fragrance in" to --fragrance is--.

In Column 14, Line 14: In Claim 15, change "benhentrimonium chloride," to --behentrimonium chloride,--.

In Column 14, Line 14: In Claim 15, change "the benhentrimonium" to --the behentrimonium--.

Signed and Sealed this  
Sixteenth Day of April, 2019

Andrei Iancu  
*Director of the United States Patent and Trademark Office*